United States Patent

Kopp et al.

(10) Patent No.: US 8,552,880 B2
(45) Date of Patent: Oct. 8, 2013

(54) GUIDED USER HELP SYSTEM FOR AN AMBULATORY INFUSION SYSTEM

(75) Inventors: Kevin Sean Kopp, Saint Paul, MN (US); Mary Ward-Welisevich, West Saint Paul, MN (US); David DeBelser, Plymouth, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 676 days.

(21) Appl. No.: 12/631,077

(22) Filed: Dec. 4, 2009

(65) Prior Publication Data

US 2011/0133946 A1    Jun. 9, 2011

(51) Int. Cl.
    G08B 21/00    (2006.01)
(52) U.S. Cl.
    USPC ..................... 340/679; 340/539.12
(58) Field of Classification Search
    USPC .......................................................... 340/679
    See application file for complete search history.

(56) References Cited

U.S. PATENT DOCUMENTS

| | | | | |
|---|---|---|---|---|
| 5,153,827 | A * | 10/1992 | Coutre et al. | 604/111 |
| 6,249,717 | B1 * | 6/2001 | Nicholson et al. | 700/241 |
| 7,967,773 | B2 * | 6/2011 | Amborn et al. | 604/19 |
| 2002/0065454 | A1 | 5/2002 | Lebel et al. | |
| 2003/0163223 | A1 | 8/2003 | Blomquist | |
| 2005/0022274 | A1 | 1/2005 | Campbell | |
| 2007/0118405 | A1 | 5/2007 | Campbell et al. | |
| 2008/0065007 | A1 | 3/2008 | Peterson | |
| 2008/0065016 | A1 | 3/2008 | Peterson | |
| 2008/0132844 | A1 | 6/2008 | Peterson | |
| 2008/0300572 | A1 | 12/2008 | Rankers | |
| 2009/0163855 | A1 * | 6/2009 | Shin et al. | 604/66 |
| 2009/0177180 | A1 | 7/2009 | Rubalcaba | |
| 2011/0087165 | A1 * | 4/2011 | Amborn et al. | 604/153 |

FOREIGN PATENT DOCUMENTS

WO    WO 2011/068648 A2    6/2011

OTHER PUBLICATIONS

PCT Search Report dated Aug. 31, 2011 for PCT Application No. PCT/US2010/056233 filed Nov. 10, 2010.
International Preliminary Report and Written Opinion for International Application No. PCT/US2010/056233 dated Jun. 5, 2012.

* cited by examiner

*Primary Examiner* — Travis Hunnings
(74) *Attorney, Agent, or Firm* — Patterson Thuente Pedersen, P.A.

(57) ABSTRACT

An ambulatory infusion pump can include a guided user help system that allows for a user to correct an error with the pump without needing to summon a home healthcare aide or other medical professional. When an error occurs with the pump, the user can select an option to receive help with the error. The help screen can display a possible solution for correcting the error that the user can follow. Additional help screens can display additional possible solutions if prior possible solution prove ineffective at correcting the problem.

13 Claims, 8 Drawing Sheets

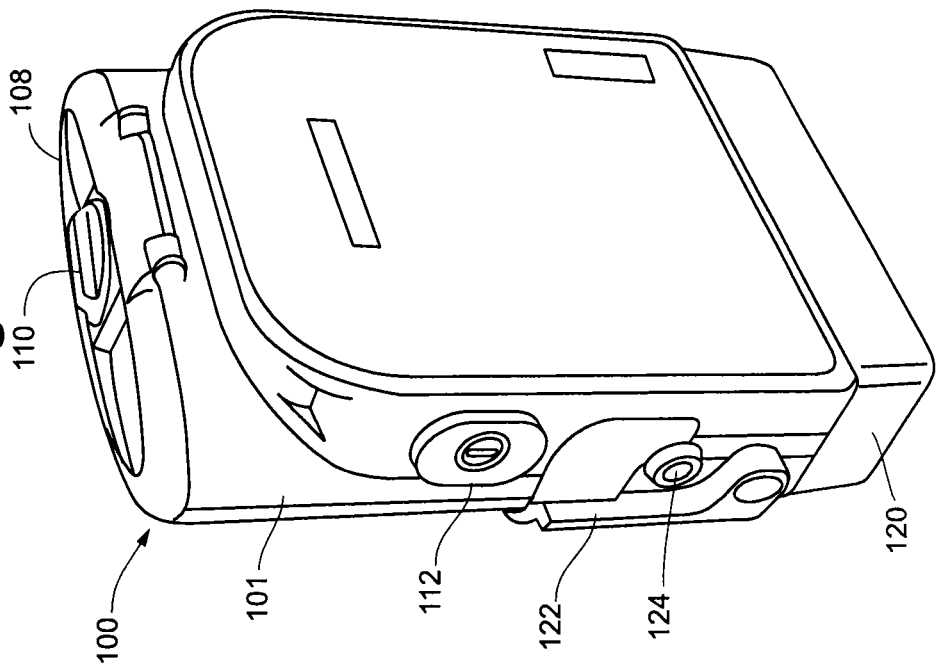
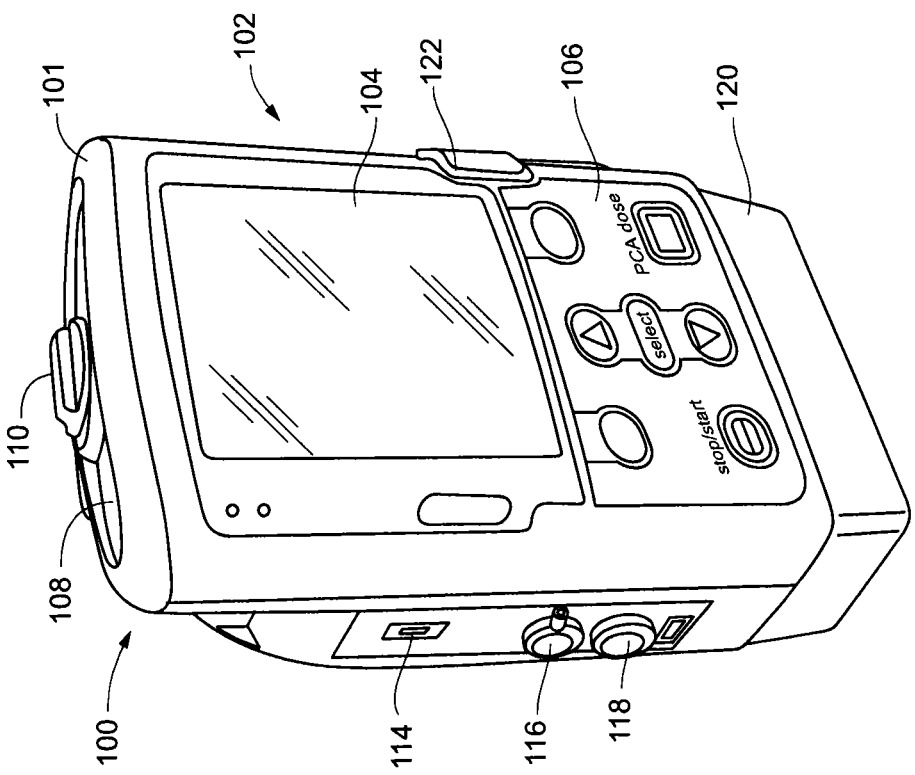

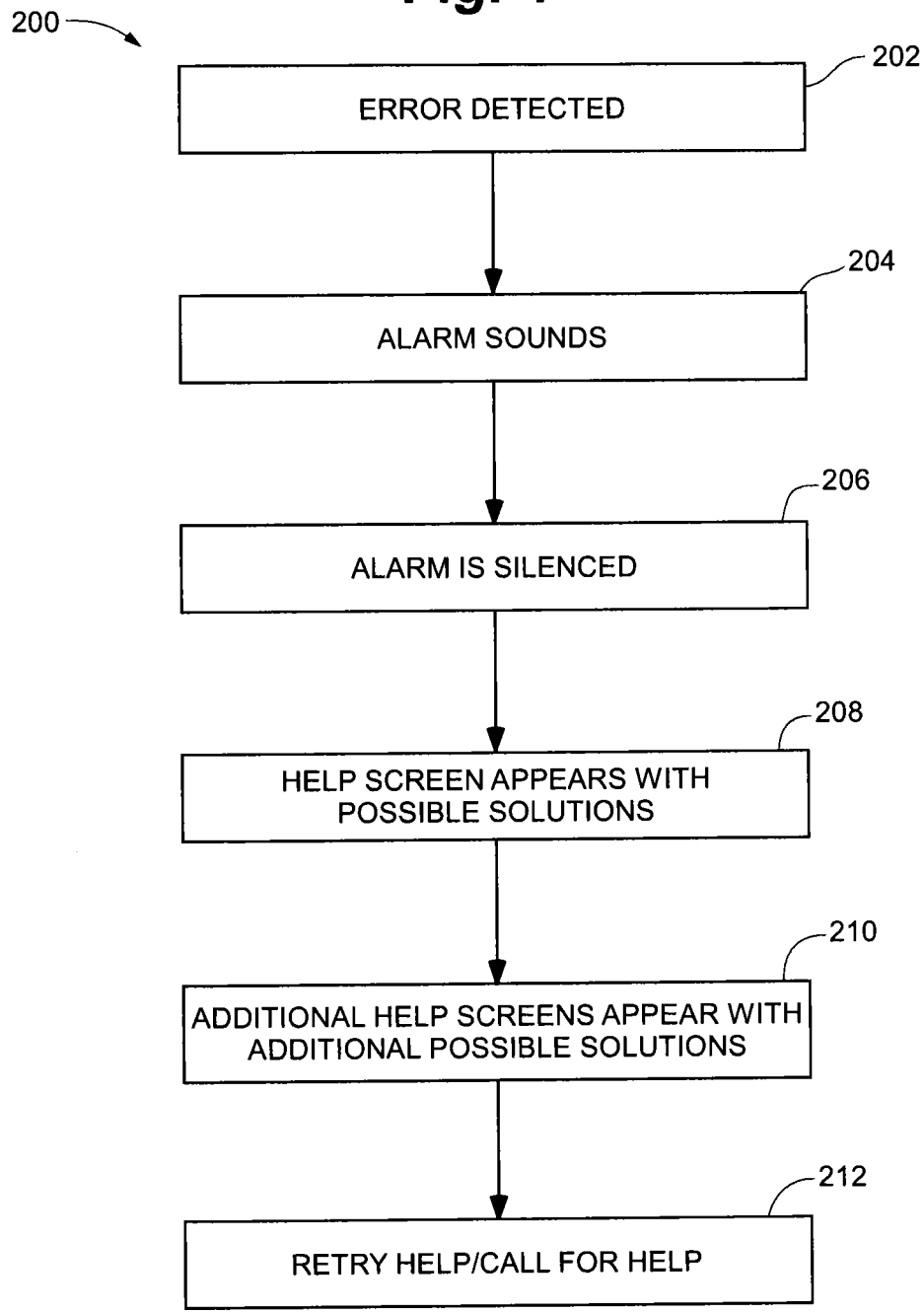

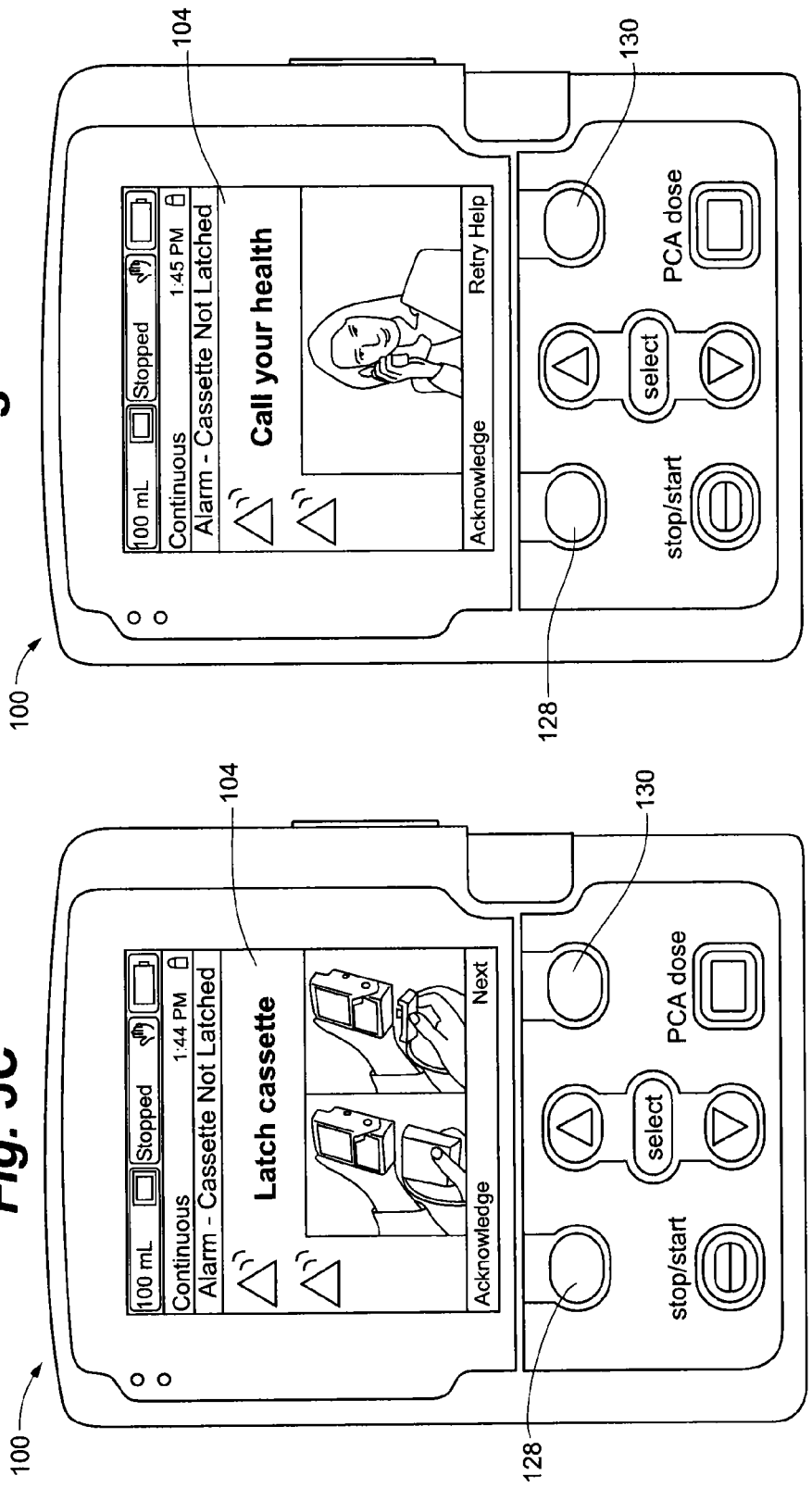

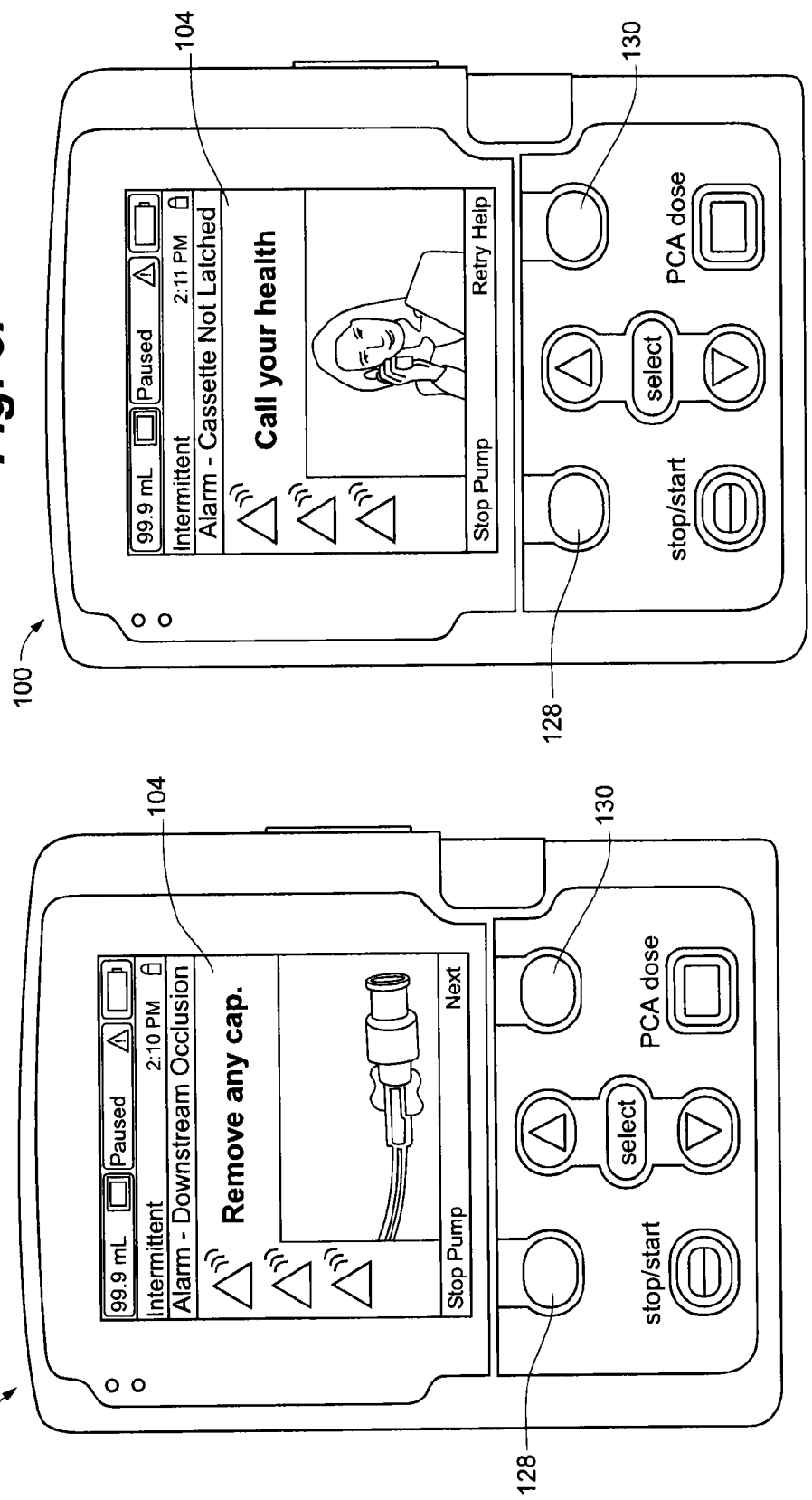

GUIDED USER HELP SYSTEM FOR AN AMBULATORY INFUSION SYSTEM

TECHNICAL FIELD

The invention relates generally to ambulatory infusion systems and more specifically to a guided user help system for an ambulatory infusion system.

BACKGROUND

Ambulatory infusion pumps are useful for providing a variety of drug therapies. Ambulatory infusion pumps can be particularly beneficial for therapies which must be delivered over an extended period of time.

Although ambulatory infusion pumps are typically used in a hospital or clinic setting, with the shift of health care delivery from the hospital setting to the outpatient and home settings, reliable effective ambulatory pumps for home use are necessary to safely deliver medications. A problem with patient home use of ambulatory infusion pumps, however, is that patients and family members are typically not professionally trained in use of the devices. Thus, if a problem arises with operation of the device, the patient is often not aware of how to correct the problem. This can require the patient to call a nurse or other outside caregiver to correct the problem, often requiring an in-person visit, or to spend significant time on the phone with a customer helpline trying to describe and correct the problem. Accordingly, there is a need for a quicker and more reliable way for patients to correct errors with ambulatory infusion pumps in a home setting.

SUMMARY OF THE INVENTION

An ambulatory infusion pump can include a guided user help system that allows for a user to correct an error with the pump without needing to summon a home healthcare aide or other medical professional. When an error occurs with the pump, the user can select an option to receive help with the error. The help screen can display a possible solution for correcting the error that the user can follow. Additional help screens can display additional possible solutions if prior possible solutions prove ineffective at correcting the problem.

In one embodiment, an ambulatory infusion system includes an infusion pump, a control system configured to control operation of the infusion pump, and a control module including a display and a control pad for operating the control system. A guided user help system can be configured to be displayed on the display and be operable with the control pad. In response to detection of an error, the guided user help system can be configured to display a possible solution to the error on the display. In some embodiments, the guided user help system can sequentially display a plurality of possible solutions.

In one embodiment, a user can be guided to correct an error with an ambulatory infusion system. First, an error with an ambulatory infusion system is identified. Next, an alarm can be provided with a control module of the ambulatory infusion system to notify the user of the error. A user may then request help in correcting the error. In response to the user request for help, a possible solution for correcting the error can be displayed on a display screen of the control module. If the user requests additional help, additional possible solutions can be displayed.

BRIEF DESCRIPTION OF THE DRAWINGS

The invention may be more completely understood in consideration of the following detailed description of various embodiments of the invention in connection with the accompanying drawings, in which:

FIG. 1 is a front perspective view of an ambulatory infusion pump according to an embodiment of the present invention.

FIG. 2 is a rear perspective view of an ambulatory infusion pump according to an embodiment of the present invention.

FIG. 4 is a flowchart of a guided user help system according to an embodiment of the present invention.

FIG. 5C is a view of an ambulatory infusion pump with a guided user help system according to an embodiment of the present invention.

FIG. 5D is a view of an ambulatory infusion pump with a guided user help system according to an embodiment of the present invention.

FIG. 6E is a view of an ambulatory infusion pump with a guided user help system according to an embodiment of the present invention.

FIG. 6F is a view of an ambulatory infusion pump with a guided user help system according to an embodiment of the present invention.

Figure 3:
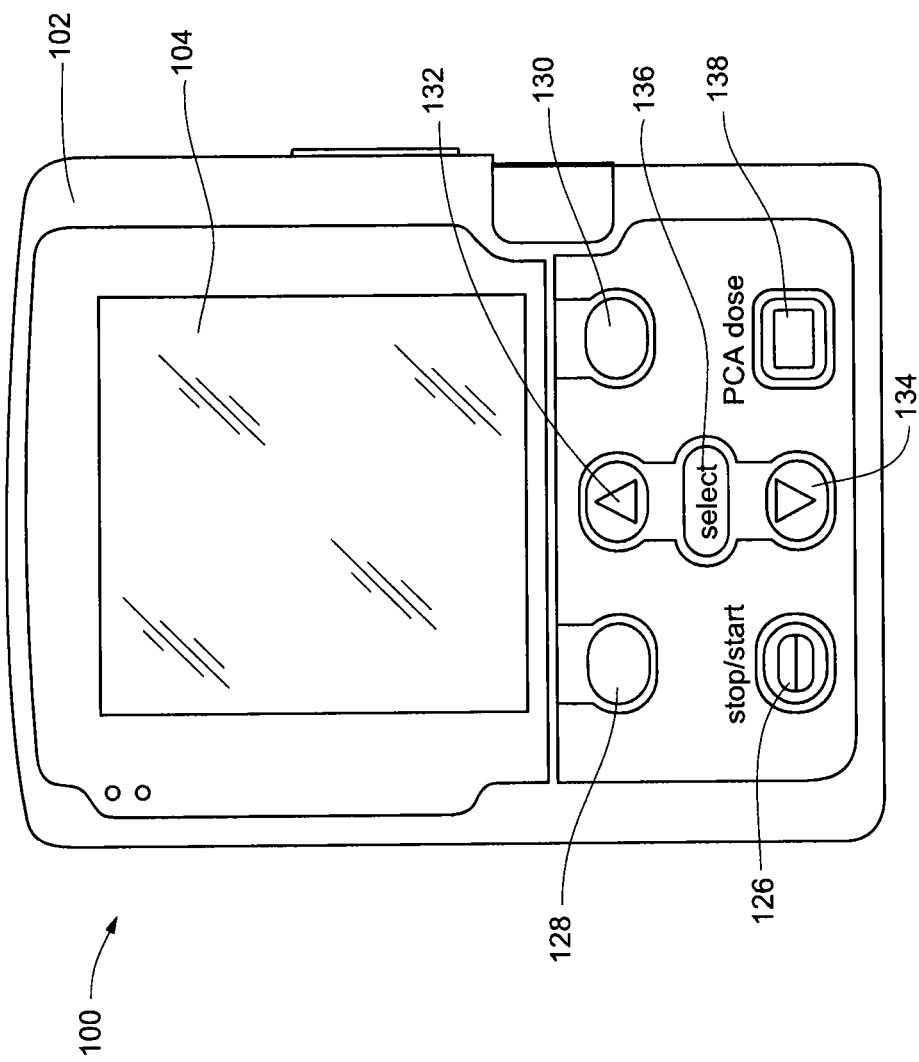
FIG. 3 is a front view of an ambulatory infusion pump according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention relates to a guided user help system for an ambulatory infusion system. In one embodiment, the ambulatory infusion system can be a CADD-Solis® Ambulatory Infusion System from Smiths Medical ASD, Inc. The ambulatory infusion system can also be of the type disclosed in commonly owned U.S. Patent Publication Nos. 2008/0065007, 2008/0065016 and 2008/0132844, assigned to Smiths Medical ASD, Inc., which are incorporated by reference herein.

An exemplary ambulatory infusion pump 100 with which a guided user help system can be used is depicted in FIGS. 1 and 2. Ambulatory infusion pump 100 includes a control system with a processor and memory programmable with selected functions for controlling operation of a pumping mechanism. Ambulatory infusion pump 100 can also include a control module 101 for relaying commands to the control system. Control module 101 can include a user interface 102 having a display screen 104 and a control pad 106. Control module 101 can also include a battery door 108, including a knob 110 for locking and unlocking the door 108, which covers a battery compartment in which batteries for powering the pump 100 can be contained. Control module 101 can also include a power switch 112 for turning pump 100 off and on, a USB port 114 for connecting pump 100 to a computer having software designed to interface with pump 100, an AC power jack 116 for connecting an AC power cord for powering pump 100, and a remote dose cord jack 118 for connecting a remote dose cord that provides an alternative way to activate patient-controlled dosing.

Infusion pump 100 can further include a replaceable cassette 120 connected to control module 101. In one embodiment, cassette 120 includes a reservoir containing the medication that is to be delivered to the patient. Tubing can extend from the cassette 120 and communicate with an infusion set or catheter to deliver the medication to the patient. The control module 101 can be used to control the flow of medication from the cassette. One example of such a cassette is the CADD® Medication Cassette Reservoir from Smiths Medical ASD, Inc. In another embodiment, cassette 120 can include tubing that interfaces with a remote medication reservoir such as an IV bag. Tubing can extend from the reservoir to the cassette and then to an infusion set or catheter, and flow of medication through the tubing can be controlled with control module 101. One example of such a cassette is part of the CADD® Administration Set from Smiths Medical ASD, Inc. A cassette latch 122 is positioned on control module 101 and is movable to allow a cassette 120 to be inserted or removed or to hold a cassette 120 in the control module 101. A cassette lock 124 can lock latch 122 in the closed position to prevent accidental unlatching and removal of the cassette 120. Cassette lock 124 can also be configured to lock the control pad 106 to prevent accidental starting, stopping or modifying of the device.

Infusion pump 100 can also include a plurality of sensors, including an air detector, a downstream occlusion sensor, an upstream occlusion sensor, and sensors to detect whether a cassette is properly inserted, latched and locked. An air detector can be used to detect if there is air in the tubing delivering the medication to the patient. A downstream occlusion is a blockage inhibiting the flow of medication between the pump and the patient and an upstream occlusion is a blockage inhibiting the flow of medication between a remote reservoir and the pump. The downstream and upstream occlusion sensors can detect whether any such occlusions are present. In one embodiment, downstream and/or upstream occlusion sensors detect occlusions by sensing the pressure and/or force present in the tubing.

Referring to FIG. 3, a user interface 102 of a control module 101 for an ambulatory infusion pump 100 according to an embodiment of the present invention is shown. As noted above, user interface 102 generally includes a display 104 and a control pad 106. In one embodiment, display 104 is a liquid crystal display (LCD). Control pad 106 can include a start/stop key 126, a pair of soft keys 128, 130, a pair of navigation keys 132, 134, a select key 136, and a PCA dose key 138. Start/stop key 126 can be used to start or stop pump delivery. Soft keys 128, 130 can be used to answer questions or select options appearing on the display 102 above the soft keys 128, 130. Navigation keys 132, 134 allow the user to scroll through menus appearing on display 102 and select key 136 allows the user to make selections from the menus. PCA dose key 138, if enabled, allows a patient to administer a patient-controlled dose of medication.

A flowchart depicting an embodiment of a guided user help system 200 of an ambulatory infusion system is depicted in FIG. 4. Initially, an error or other alert condition is detected at 202, triggering an alarm or other notification to sound and/or be displayed at 204. Errors can be detected by, for example, any of the above-described sensors. Other errors or alert conditions can also be detected by other devices or portions of pump 100. In some embodiments, the user can then silence or clear the alarm at 206.

Next, the user can enter a guided user help system, beginning with a first help screen at 208. The help screen can provide a possible solution to the user for correcting the particular error, alert or condition detected by pump 100. In one embodiment, the guided user help system presents a user with a series of possible solutions to the detected error. The possible solutions displayed can relate to the most common reasons for occurrence of the particular error. The user may then have the option of viewing additional help screens displaying additional possible solutions for correcting the error at 210. In one embodiment, help screens are displayed in order of the most likely cause of the particular error.

Once all available help screens have been viewed, at 212 a screen providing the user with the option of reentering the help screens and/or providing a customized support message can be displayed. This can be of use if a user goes through all available help screens without successfully clearing the error condition. Customized support message can include, for example, a number of a customer helpline or a number of a home healthcare aide assigned to the patient. The customized support message can also include an email address, a uniform resource locator (URL) or the name or an individual or organization to contact. If at any time during the sequence the user is able to correct the error by following the help screens, the guided user help system can be automatically or manually exited and the pump can automatically or manually be returned to its normal functioning. Operation of the guided user help system according to embodiments of the present invention is further described with reference to FIGS. 5A-5D and 6A-6F.

Figure 5A:
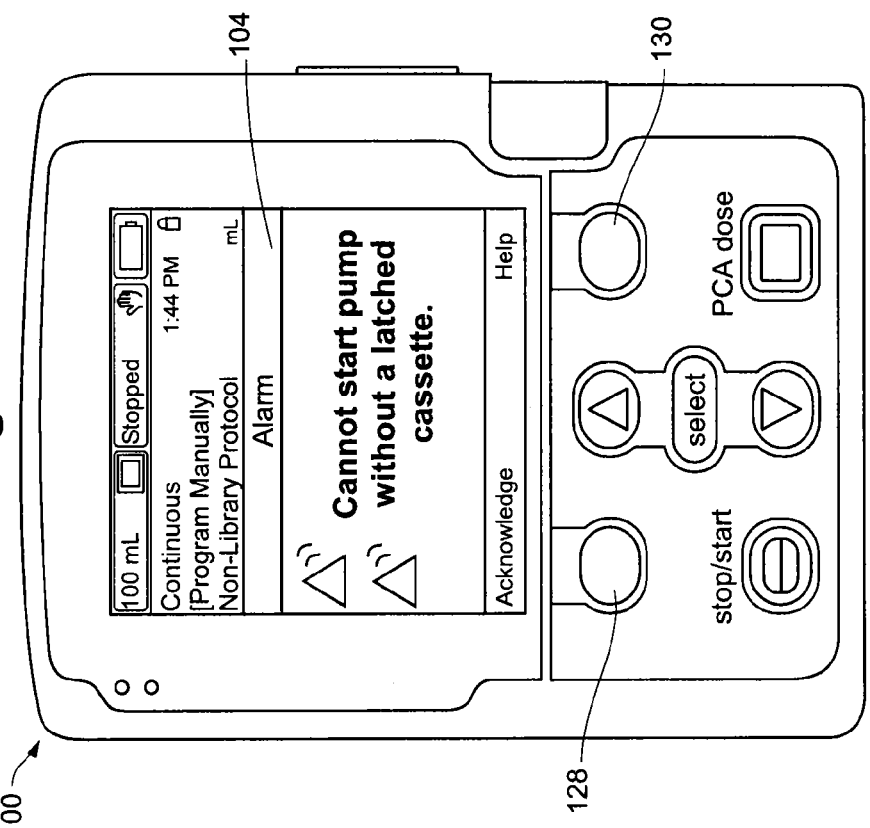
FIG. 5A is a view of an ambulatory infusion pump with a guided user help system according to an embodiment of the present invention.
Figure 5B:
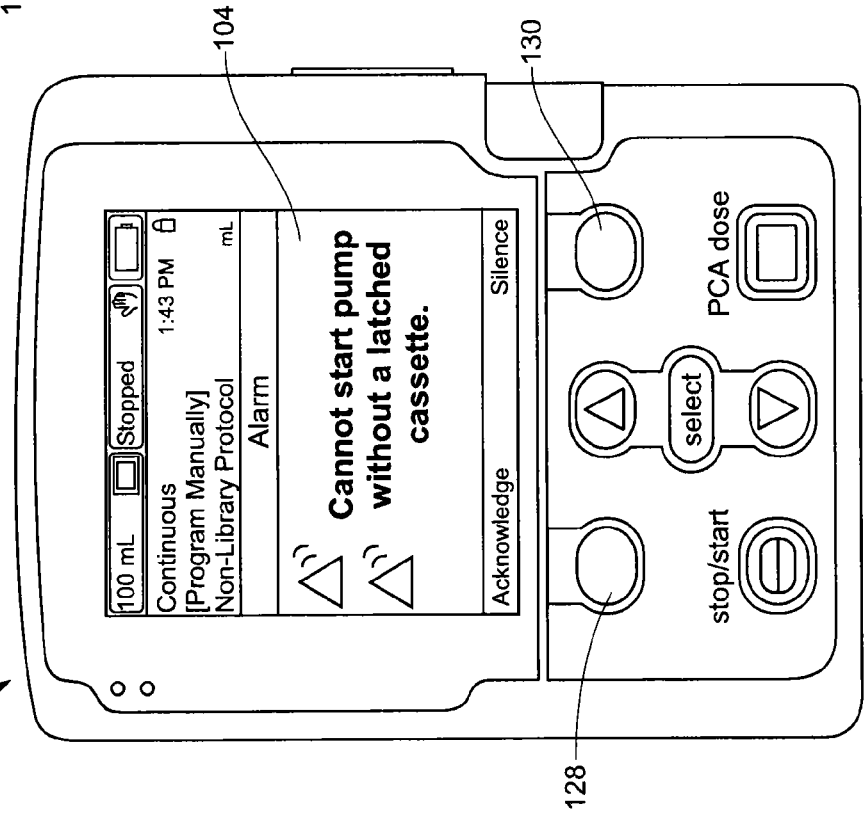
FIG. 5B is a view of an ambulatory infusion pump with a guided user help system according to an embodiment of the present invention.

FIGS. 5A-5D depict operation of a guided user help system in response to an error caused by a cassette 120 that is not latched. In FIG. 5A, the error of the unlatched cassette is detected and an alarm alerting the user of the error is depicted both visually on display 104 and audibly. The user then has the option of pressing the right soft key 130 to silence the audible alarm or the left soft key 128 to acknowledge the alarm and exit the alarm screen. This provides the user the option of opting out of the guided user help system in order to manually correct the problem. This feature is useful for users who are experienced with the device and do not need to be provided with possible solutions for correcting the error. If the user presses the right soft key 130 to silence the alarm, an option to view a help screen appears as in FIG. 5B. This option can be selected with the right soft key 130.

If the user selects the help option, a user help screen appears on the display 104 as shown in FIG. 5C. User help screen displays a possible solution for correcting the error and can use textual and/or graphical ways of disclosing the possible solution. In this example, the possible solution is simply to latch the cassette. If the user is able to properly latch the cassette, the alarm can automatically turn off when the error is corrected. If unable to latch the cassette, the user can select the right soft key 130 to view the next screen. In this example, the system does not have any additional possible solutions to suggest, so a customized support message can be shown on the display 104 as depicted in FIG. 5D. The user can return to the help screen by selecting "Retry Help" with the right soft key 130. The user can acknowledge the alarm from the customized support message in FIG. 5D (or from the help screen in FIG. 5C) by selecting the left soft key 128, allowing the user to correct the problem outside of the guided user help system. The customized support message can be customized for the specific patient or for the organization or healthcare facility supporting the pump to display a phone number for a customer helpline, home healthcare aide, or other service provider that the user can call for further information/help.

Figure 6A:
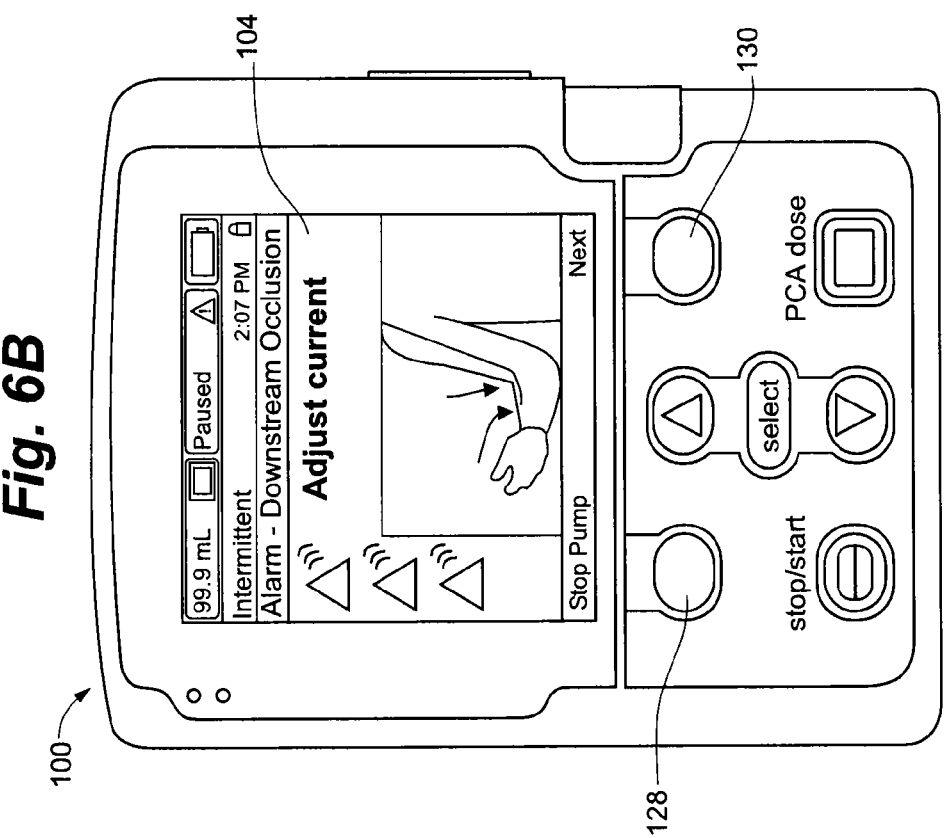
FIG. 6A is a view of an ambulatory infusion pump with a guided user help system according to an embodiment of the present invention.
Figure 6B:
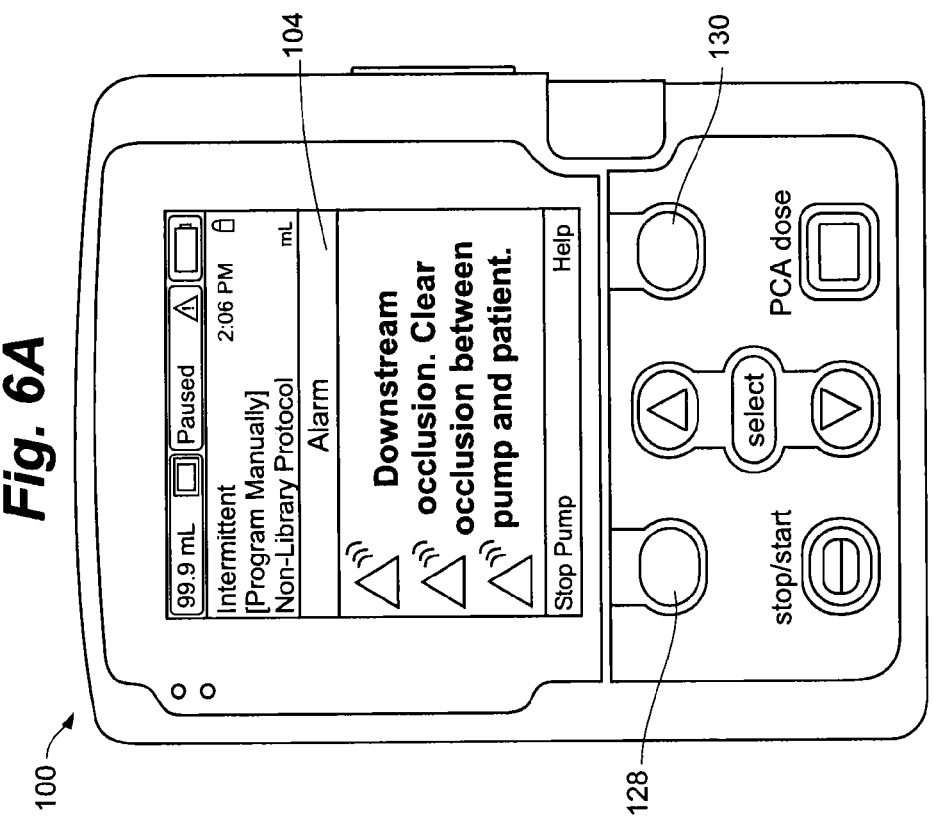
FIG. 6B is a view of an ambulatory infusion pump with a guided user help system according to an embodiment of the present invention.
Figures 6C, 6D:
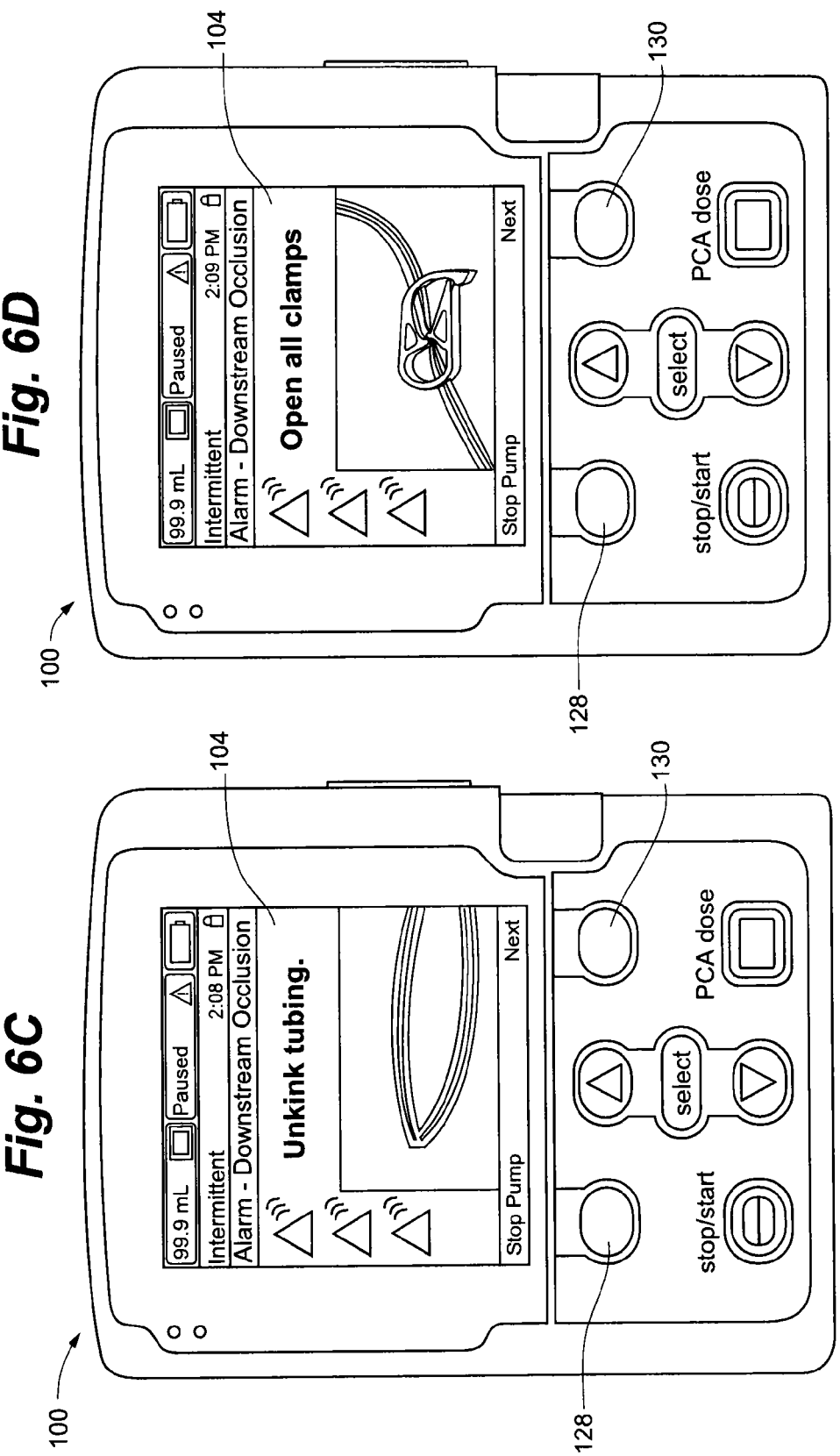
FIG. 6C is a view of an ambulatory infusion pump with a guided user help system according to an embodiment of the present invention.
FIG. 6D is a view of an ambulatory infusion pump with a guided user help system according to an embodiment of the present invention.

FIGS. 6A-6F depict operation of a guided user help system in response to a downstream occlusion detected by downstream occlusion sensor during operation of the pump. As shown in FIG. 6A, after the user has silenced the alarm the user can opt to view a help screen by selecting the right soft key 130. At any point during the process, the user can elect to stop the pump by selecting the left soft key 128. FIG. 6B displays a first help screen that provides a possible solution to the user of adjusting the current. If this removes the occlusion, the infusion pump 100 can automatically return to the pumping operation. If the occlusion continues, the user can select "Next" with the right soft key 130. A second help screen then appears as in FIG. 6C. This help screen suggests the possible solution of unkinking the tubing. Additional help screens that the user can navigate to with the right soft key 130 are depicted in FIGS. 6D and 6E that suggest possible solutions of opening clamps and removing a cap on the end of the tubing. If at any point during the process the possible solution removes the occlusion, the alarm can automatically terminate and the pump can resume normal operation. Once the user has cycled through all of the available help screens, the customized support message can be displayed, as shown in FIG. 6F, allowing the user to reenter the help screens and providing the user with a number to call for additional help.

Guided user help system as described above can be employed with any other error/alarm messages that are applicable to an ambulatory infusion system. Guided user help system provides a non-professionally trained user with possible solutions for correcting errors without needing to summon a home healthcare aide or other medical professional. The system can be employed with all alarms applicable to an ambulatory infusion pump, or can be provided with just some of the alarms. Examples of other alarms/errors with which guided user help system can be employed include: air in the tubing, an upstream occlusion, errors related to operation of the pumping mechanism, errors related to the battery or other power supply, improper treatment delivery settings, lack of medication in the reservoir, an improper cassette, the cassette not properly loaded or locked, improper key insertion, errors with a PCA dose cord or other external attachment, and one or more faulty sensors, among others.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An ambulatory infusion pump assembly for delivering a fluid from a fluid reservoir to an infusion set adapted for the subcantaneous infusion of the fluid into the body of a patient, the operation of said pump assembly presenting at least one measurable pump assembly operating parameter having a predetermined normal operating value, the pump assembly, comprising:
   a pump mechanism;
   an upstream delivery line operably coupling the pump mechanism to said fluid reservoir in fluid conveying relationship;
   a downstream delivery tube operably coupling the pump mechanism to said infusion set in fluid conveying relationship;
   a control system configured to control operation of the pump assembly;
   at least one sensor operably coupled with said control system, the sensor adapted for sensing the value of said at least one pump assembly operating parameter of said pump assembly;
   a user interface including a display and a control pad operably coupled to the control system and adapted for interactive operation of said pump assembly;
   the control system further including a guided user help system configured to present an alarm when said at least one sensor senses the value of said at least one pump assembly operating parameter to be outside of said predetermined normal operating value, and to present on the display a control system guided procedure, adapted to correct said at least one operating parameter back to said predetermined normal operating value.

2. The system of claim 1, wherein the guided user help system is configured to display a plurality of procedures.

3. The system of claim 2, wherein the plurality of possible procedures are displayed sequentially.

4. The system of claim 3, wherein the plurality of possible procedures are sequentially displayed beginning with a most common possible solution.

5. The system of claim 3, wherein the sequence of the plurality of possible procedures is advanced via input to the control pad.

6. The system of claim 1, wherein the guided user help system displays the possible procedure only after receiving a request from a user for help in correcting the operating parameter value.

7. The system of claim 1, wherein the guided user help system displays the possible procedure that is a most common solution for correcting the operating parameter value.

8. The system of claim 1, wherein the guided user help system is further configured to display a customized support message if the operating parameter value is not corrected.

9. The system of claim 8, wherein the customized support message comprises at least one of a telephone number, an email address, a contact name, or a URL.

10. The system of claim 1, further comprising a cassette including a reservoir containing medication, the cassette attached to the control module with a latch and selectively lockable with the control module, and wherein the operating parameter is detected by a sensor selected from the group consisting of: a cassette insertion sensor, a cassette latch sensor and a cassette lock sensor.

11. The system of claim 1, further comprising tubing for delivering medication to a patient, and wherein the operating parameter is detected by a sensor selected from the group consisting of: a downstream occlusion sensor, an upstream occlusion sensor, and an air detector.

12. The system of claim 1, wherein the guided user help system is configured to automatically stop displaying if the operating parameter is corrected.

13. The system of claim 1, wherein the operating parameter relates to an error from the group consisting of: air in tubing; an occlusion; an error related to an operation of a pumping mechanism of the infusion pump; an error related to a battery or power supply; an error related to an improper treatment delivery setting; a low or lack of medication in a reservoir of the infusion pump; an improper medication cassette; an improperly loaded medication cassette; an unlocked medication cassette; an improper key insertion; an error related to a PCA dose cord; an error related to an external attachment to the infusion pump; and an error related to a sensor.

* * * * *

UNITED STATES PATENT AND TRADEMARK OFFICE
CERTIFICATE OF CORRECTION

| | | |
|---|---|---|
| PATENT NO. | : 8,552,880 B2 | Page 1 of 1 |
| APPLICATION NO. | : 12/631077 | |
| DATED | : October 8, 2013 | |
| INVENTOR(S) | : Kopp et al. | |

It is certified that error appears in the above-identified patent and that said Letters Patent is hereby corrected as shown below:

In the Claims

<u>Claim 1, Column 6, Line 29</u>:
Delete "subcantaneous" and insert -- subcutaneous --.

Signed and Sealed this
Twenty-ninth Day of July, 2014

Michelle K. Lee
*Deputy Director of the United States Patent and Trademark Office*